(12) United States Patent
Mirza et al.

(10) Patent No.: US 11,006,970 B2
(45) Date of Patent: May 18, 2021

(54) ENDOSCOPIC SURGICAL BLADE AND METHOD OF USE THEREOF

(71) Applicant: A.M. SURGICAL, INC., Smithtown, NY (US)

(72) Inventors: Ather Mirza, Smithtown, NY (US); Romi Mirza, Smithtown, NY (US)

(73) Assignee: A.M. Surgical, Inc., Smithtown, NY (US)

( * ) Notice: Subject to any disclaimer, the term of this patent is extended or adjusted under 35 U.S.C. 154(b) by 52 days.

(21) Appl. No.: 16/594,548

(22) Filed: Oct. 7, 2019

(65) Prior Publication Data

US 2020/0029995 A1      Jan. 30, 2020

Related U.S. Application Data

(63) Continuation of application No. 15/670,604, filed on Aug. 7, 2017, now Pat. No. 10,478,210, which is a continuation of application No. 14/521,248, filed on Oct. 22, 2014, now abandoned, which is a continuation of application No. 13/559,303, filed on Jul. 26, 2012, now Pat. No. 9,144,433.

(51) Int. Cl.
    *A61B 17/32*       (2006.01)
(52) U.S. Cl.
    CPC .......................... *A61B 17/320036* (2013.01)
(58) Field of Classification Search
    CPC .... A61B 17/320016; A61B 17/320036; A61B 2017/320052
    See application file for complete search history.

(56) References Cited

U.S. PATENT DOCUMENTS

| | | |
|---|---|---|
| 5,323,765 A | 6/1994 | Brown |
| 5,346,503 A | 9/1994 | Chow |
| 5,366,465 A | 11/1994 | Mirza |
| 9,131,951 B2 | 9/2015 | Mirza et al. |
| 9,144,433 B2 | 9/2015 | Mirza et al. |
| 2004/0098005 A1 | 5/2004 | Mirza et al. |
| 2010/0069936 A1 | 3/2010 | Palmer et al. |
| 2011/0130779 A1 | 6/2011 | Mirza et al. |

OTHER PUBLICATIONS

File History of U.S. Appl. No. 13/559,303, filed Jul. 26, 2012.
File History of U.S. Appl. No. 14/521,248, filed Oct. 22, 2014.
File History of U.S. Appl. No. 15/670,604, filed Aug. 7, 2017.
U.S. Appl No. 13/559,303, filed Jul. 26, 2012, Patented.
U.S. Appl. No. 14/521,248, filed Oct. 22, 2014, Abandoned.
U.S. Appl. No. 15/670,604, filed Aug. 7, 2017, Pending.

*Primary Examiner* — Ryan J. Severson
(74) *Attorney, Agent, or Firm* — Bodner & O'Rourke, LLP; Gerald T. Bodner; Christian P. Bodner

(57) ABSTRACT

An endoscopic surgical blade having a low-profile design, with an upper cutting surface and a lower cutting surface at its distal end and having a non-cutting radiused surface at the top end of the upper cutting surface, and the upper cutting surface and lower cutting surface meet at a crotch therebetween is disclosed. The blade is part of an endoscopic knife assembly which also contains a hollow knife tube hollow that allows the insertion of an endoscope for viewing of the surgical procedure. The endoscopic knife assembly can be used for in endoscopic surgery by insertion of the assembly through a slotted cannula. A method for a performing an operative procedure on a target tissue in a subject using the endoscopic knife assembly having a low-profile blade with an upper cutting surface and a lower cutting surface is also described.

14 Claims, 5 Drawing Sheets

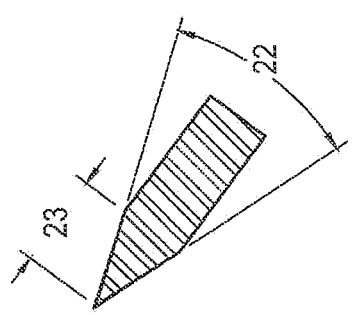
FIG. 2B
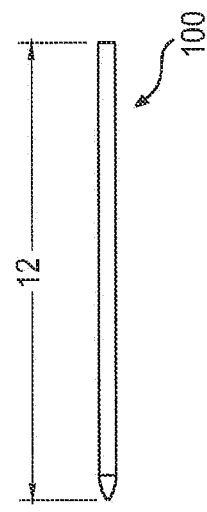
FIG. 2C
FIG. 2D
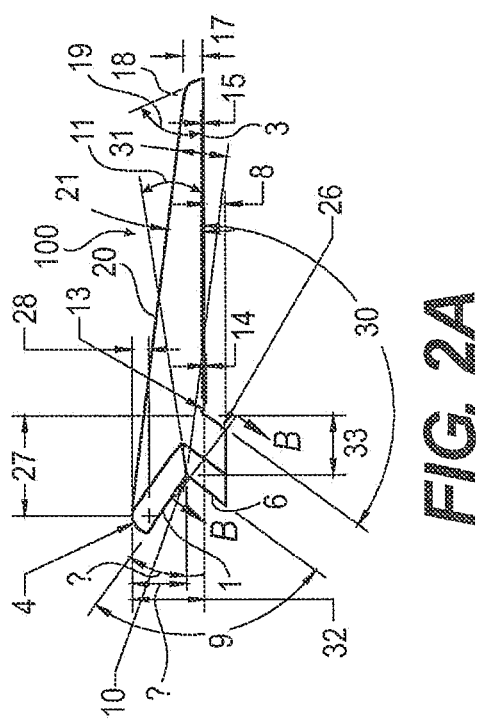
FIG. 2A
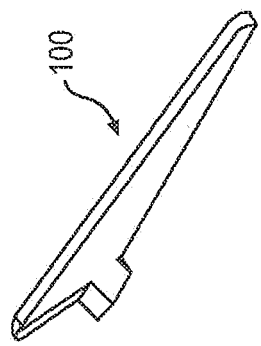
FIG. 2E

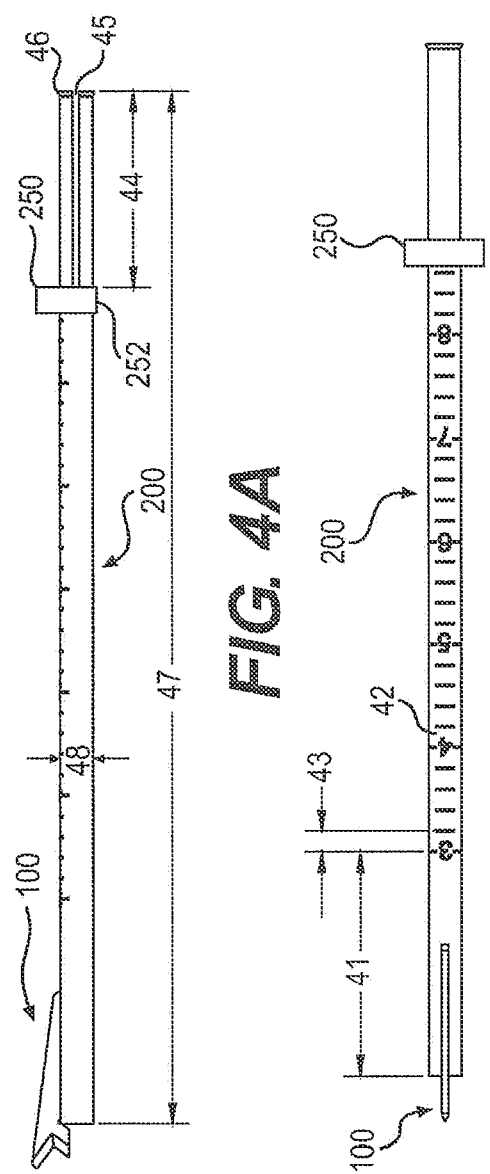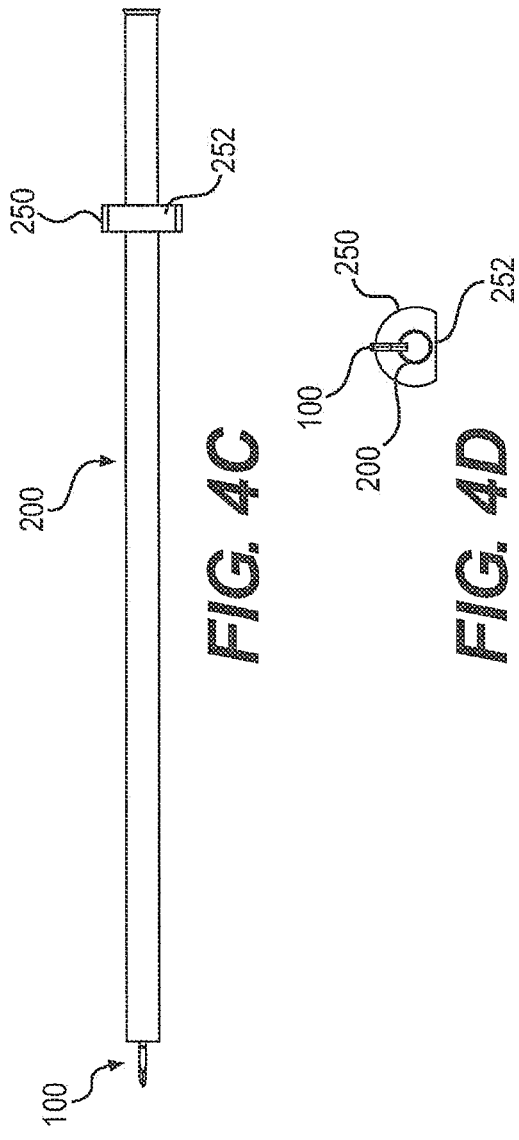

ENDOSCOPIC SURGICAL BLADE AND METHOD OF USE THEREOF

This application is a Continuation of U.S. application Ser. No. 15/670,604, filed Aug. 7, 2017, which is a Continuation of U.S. application Ser. No. 14/521,248, filed Oct. 22, 2014, which is a Continuation of U.S. application Ser. No. 13/559,303, filed Jul. 26, 2012, now U.S. Pat. No. 9,144,433. The entirety of the aforementioned application is incorporated herein by reference.

FIELD

This application generally relates to medical devices. In particular, the application relates to devices and methods for endoscopic surgery, e.g., for endoscopic trigger release surgery.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Trigger finger is characterized by catching, snapping or locking of the involved finger flexor tendon, associated with dysfunction and pain. Localized inflammation or nodular swelling of said flexor tendon causes a disparity in size between the flexor tendon and the surrounding retinacular pulley system, most commonly at the level of the first annular (A1) pulley. When the subject extends the involved finger, the tendon will "catch" on the pulley, followed by an abrupt popping of the tendon through the pulley. This results in a difficulty flexing or extending the finger and the "triggering" phenomenon.

Typically, a first course of treatment for trigger finger is corticosteroid injections into the tendon sheath to reduce inflammation. When corticosteroid injection is not or no longer effective, surgical division of the A1 pulley is indicated. Conventional surgical techniques for trigger finger release require a fairly large incision over the A1 pulley and spreading of the incision to allow viewing and instrument access. These techniques can require a longer period of recovery than endoscopic methods and have greater levels of post-operative pain due to the incision size and level of manipulation during the procedure. Previous endoscopic techniques for trigger finger release require two incisions, one proximal and one distal to the A1 pulley and the threading of a cannula through the two incisions. An arthroscope is then inserted in the distal end of the cannula, while a cutting tool is inserted in the proximal opening. The cutting tool and arthroscope are then alternately moved forward or backward through the cannula. This does not allow direct visualization of the procedure from the point of view of the cutting tool during the separation of the pulley. Accordingly, the present application fulfils a need in the art for a minimally invasive surgical procedure for the treatment of trigger finger by providing a method for uniportal endoscopic trigger release surgery and a low-profile endoscopic surgical blade with a downward oriented blade having two forward facing cutting surfaces.

SUMMARY

One aspect of the present application relates to a low-profile blade for an endoscopic knife assembly, comprising an upper cutting surface and a lower cutting surface at its distal end and having a non-cutting radiused surface at the top end of the upper cutting surface, wherein said upper cutting surface and said lower cutting surface meet at a crotch therebetween, wherein the blade is sized to fit at a tip of an endoscope.

Another aspect of the present application relates to an endoscopic knife assembly, comprising: a knife tube having a distal end and a proximate end and a low-profile blade comprising an upper cutting surface and a lower cutting surface at its distal end and having a non-cutting radiused surface at the top end of the upper cutting surface, wherein said upper cutting surface and said lower cutting surface meet at a crotch therebetween.

Another aspect of the present application relates to an instrument kit for implementing an endoscopic surgical procedure comprising: an endoscopic knife assembly comprising a low-profile blade comprising an upper cutting surface and a lower cutting surface at its distal end and having a non-cutting radiused surface at the top end of the upper cutting surface, wherein said upper cutting surface and said lower cutting surface meet at a crotch therebetween.

Another aspect of the present application relates to a method for treating trigger finger, comprising: establishing an entry portal at a location proximal to A1 pulley; inserting a cannula having open proximal and distal ends and an open slot extending along the length of the cannula; inserting an endoscope into the cannula, said endoscope comprising an endoscopic knife assembly having a low-profile blade comprising an upper cutting surface and a lower cutting surface at its distal end and having a non-cutting radiused surface at the top end of the upper cutting surface, wherein said upper cutting surface and said lower cutting surface meet at a crotch therebetween; advancing said endoscope so that the blade moves in contact with the A1 pulley through the slot; operatively engaging the A1 pulley with the blade; and advancing the blade through the cannula to divide the A1 pulley.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

FIG. 1A depicts a side view of the blade component, showing the cutting surfaces, the transition where the blade is joined to a knife tube and the taper at the end of the blade. FIG. 1B is a cross section view of the blade at the bisecting line A-A in FIG. 1A depicting an exemplary angle of a cutting surface of the blade component. FIG. 1C is a perspective view of the blade from the front depicting the width of the blade and the cutting surfaces.

FIGS. 2A-E illustrate alternate features of a blade component of an endoscopic knife assembly.

FIG. 3A is a perspective view of the endoscopic knife assembly from the side. FIG. 3B is a perspective view of the endoscopic knife assembly from the top. FIG. 3C is a perspective view of the endoscopic knife assembly from the bottom. FIG. 3D is a perspective view of the endoscopic knife assembly from the distal end. FIG. 3D is a perspective view of the endoscopic knife assembly from the distal end. FIG.

3E is a perspective view of the endoscopic knife assembly from the proximate end. FIG. 3F is a perspective view of the endoscopic knife assembly from an angle.

FIGS. 4A-E illustrate an endoscopic knife assembly. FIG. 4A is a perspective view of the endoscopic knife assembly from the side. FIG. 4B is a perspective view of the endoscopic knife assembly from the top. FIG. 4C is a perspective view of the endoscopic knife assembly from the bottom. FIG. 4D is a perspective view of the endoscopic knife assembly from the distal end. FIG. 4D is a perspective view of the endoscopic knife assembly from the distal end. FIG. 4E is a perspective view of the endoscopic knife assembly from an angle.

DETAILED DESCRIPTION

Figure 1A:
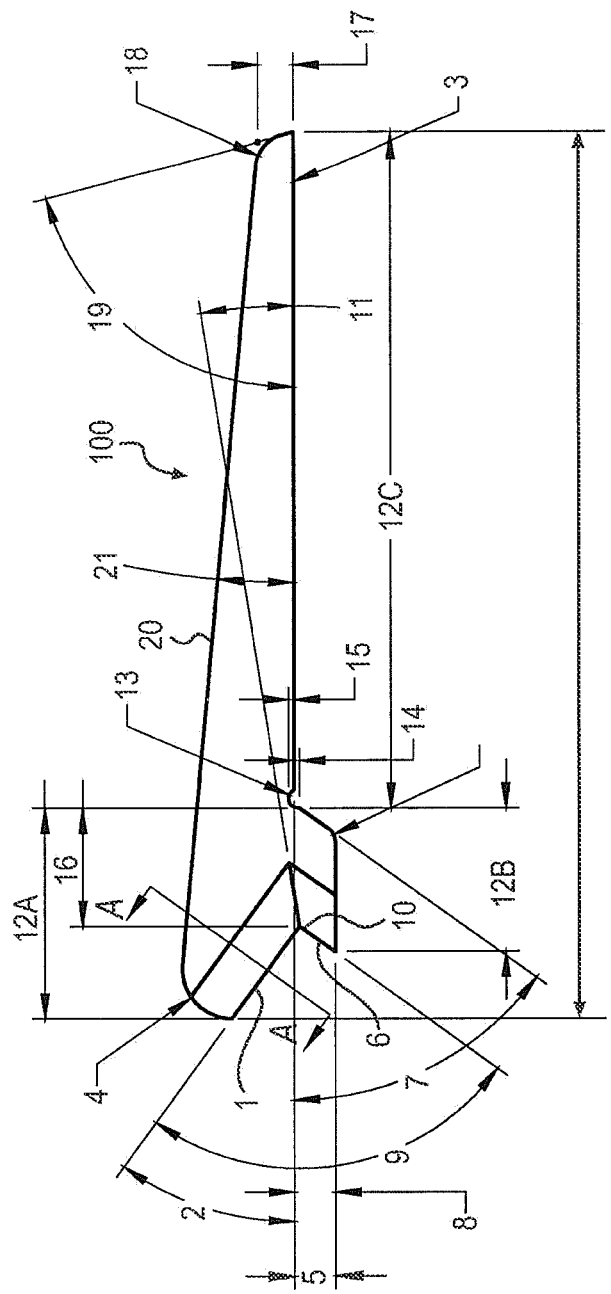
FIGS. 1A-C illustrate a blade component of an endoscopic knife assembly.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

The term "trigger finger," as used herein, also refers to "trigger digit," "trigger thumb," and "stenosing tendovaginitis."

The blade described herein is a low-profile blade that has a downward angled first cutting surface that is radiused at its upper end to prevent damage to the underlying tendon during the separation of the A1 pulley. The blade further has an upward angled second cutting surface that captures the A1 pulley and directs it into the crotch of the blade for cutting. In some embodiments, the crotch of the blade is below the plane of where the blade mounts onto a knife tube, such that the cutting of the pulley is visualized directly in front of an arthroscope inserted through the endoscopic knife assembly during a procedure. In other embodiments, the crotch of the blade is above the plane of where the blade mounts onto a knife tube. Additionally, the angle of the grind of the crotch is generally directed downward. Further, the sloped top surface allows the blade described herein to maintain a low profile such that it can be used with a slotted cannula for the precise division of the A1 pulley and to be easily withdrawn again from the tissue without damaging other tissues.

One aspect of the present application relates to a low-profile blade for an endoscopic knife assembly, comprising an upper cutting surface and a lower cutting surface at its distal end and having a non-cutting radiused surface at the top end of the upper cutting surface, wherein said upper cutting surface and said lower cutting surface meet at a crotch therebetween, further wherein the blade is sized to fit at a tip of an endoscope.

In one embodiment, the low-profile blade further comprises a horizontal mounting surface for affixing the blade onto a knife tube to form said endoscopic knife assembly.

In another embodiment, the crotch is below the plane defined by said horizontal mounting surface.

In another embodiment, the crotch is above the plane defined by said horizontal mounting surface.

In another embodiment, the top surface of the blade is angled downward towards the proximate end of the blade.

In another embodiment, the upper cutting surface is angled about 30-40 degrees from a horizontal plane running through the crotch.

In another embodiment, the upper cutting surface is angled about 36 degrees from a horizontal plane running through the crotch.

In another embodiment, the lower cutting surface is angled about 50-60 degrees from a horizontal plane running through the crotch.

In another embodiment, the lower cutting surface is angled about 54 degrees from a horizontal plane running through the crotch.

In another embodiment, the blade body comprises a notch on the lower edge to engage with a knife tube.

In another embodiment, the upper cutting surface and the lower cutting surface meet at a downward angle at the crotch.

Another aspect of the present application relates to an endoscopic knife assembly, comprising: a knife tube having a distal end and a proximate end and a low-profile blade comprising an upper cutting surface and a lower cutting surface at its distal end and having a non-cutting radiused surface at the top end of the upper cutting surface, wherein said upper cutting surface and said lower cutting surface meet at a crotch therebetween.

In one embodiment, the endoscopic knife assembly further comprising a handle at the proximal end of the knife tube.

In another embodiment, the knife tube comprises an alignment ring attached near the proximate end and one or more slots at the proximate end for the attachment of a locking assembly to the knife tube and alignment ring.

In another embodiment, the knife tube is marked on the top or side surface with gradations.

In another embodiment, the blade is welded to the knife tube.

Another aspect of the present invention relates to an instrument kit for implementing an endoscopic surgical procedure comprising: an endoscopic knife assembly comprising a low-profile blade comprising an upper cutting surface and a lower cutting surface at its distal end and having a non-cutting radiused surface at the top end of the upper cutting surface, wherein said upper cutting surface and said lower cutting surface meet at a crotch therebetween.

In one embodiment, the endoscopic knife assembly further comprises a handle at the proximal end of the knife tube.

In another embodiment, the knife tube comprises an alignment ring attached near the proximate end and one or more slots at the proximate end for the attachment of a locking assembly to the knife tube and alignment ring.

In another embodiment, the instrument kit further comprises a cannula having an open slot extending along the length of the cannula. In a related embodiment, the cannula is a clear cannula. In another related embodiment, the cannula has an inner diameter of between about 2.4 mm and about 3.0 mm. In a further embodiment, the cannula has an inner diameter of about 2.7 mm. In a separate related embodiment, the cannula has an inner diameter of between about 3.7 mm and about 4.3 mm. In a further embodiment, the cannula has an inner diameter of about 4.0 mm.

In another embodiment, the instrument kit further comprises an obturator, an elevator and/or an arthroscope.

Another aspect of the present invention relates to a method for treating trigger finger, comprising: establishing an entry portal at a location proximal to A1 pulley; inserting a cannula having open proximal and distal ends and an open slot extending along the length of the cannula; inserting an endoscope into the cannula, said endoscope comprising an endoscopic knife assembly having a low-profile blade comprising an upper cutting surface and a lower cutting surface at its distal end and having a non-cutting radiused surface at the top end of the upper cutting surface, wherein said upper cutting surface and said lower cutting surface meet at a crotch therebetween; advancing said endoscope so that the blade moves in contact with the A1 pulley through the slot; operatively engaging the A1 pulley with the blade; and advancing the blade through the cannula to divide the A1 pulley.

In one embodiment, the step of inserting an endoscope comprising an endoscopic knife assembly is preceded by the insertion of another endoscope to visualize anatomic structures surrounding the cannula.

The presently described low-profile blade is sized to fit at the tip of an endoscope and form a component of an endoscopic knife assembly, wherein the blade is welded onto a hollow knife tube that allows the practitioner to extend an endoscopic camera through the hollow knife tube to allow direct visualization of the tissue and blade before, during and after the cutting of the target tissue.

Particular embodiments of the endoscopic knife assembly further comprise a handle at its proximal end that allows the direct manual manipulation of the endoscopic knife assembly. The handle also comprises a hollow lumen that allows an arthroscope to be passed through the handle into the knife tube, allowing direct visualization of the tissue and blade before, during and after the cutting of the target tissue. Other embodiments of the knife tube assembly comprise an alignment ring and slots at the proximate end to allow the knife tube assembly to be mated with the locking mechanism of an endoscopic surgical system.

The design of the present blade is such that it is usable in endoscopic surgery in a manner that allows the practitioner to extend the blade through the cannula to the target tissue without damage to surrounding tissue and/or organs. The blade is made from materials commonly used for surgical blades or scalpels, such materials include, but are not limited to, hardened and tempered steel, stainless steel, high carbon steel, titanium, alloys and ceramic.

In particular embodiments, the blade is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the blade is made from Hitachi GIN-5 SST-MODIFIED 440-A stainless steel. The blade is optionally flash electropolished. The cutting edges are machine finished and must be sharp. In a particular embodiment, the steel of the blade is heat-treated to Rockwell C hardness of about 50-72. In a more particular embodiment, the steel of the blade is heat-treated to Rockwell C hardness of 58-64.

FIG. 1A depicts a side view of an embodiment the blade component of the endoscopic knife assembly, showing the upper and lower cutting surfaces at the leading end of the blade, the transition where the blade is joined to the knife tube and the taper at the trailing end of the blade.

Figure 1C:
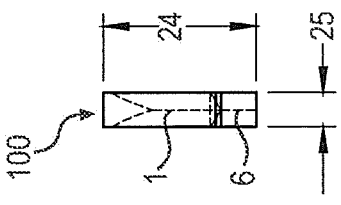
Figure 1B:
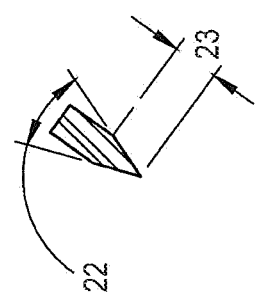

FIG. 1B is an view depicting an exemplary angle of the cutting surface of the blade as viewed from the perspective of the line A-A in FIG. 1A.

FIG. 1C is a perspective view of the blade in FIG. 1A from the front depicting the height and width of the blade.

In a particular embodiment, the blade 100 as shown in FIG. 1A comprises an upper cutting surface 1 on the leading end of the blade, which is at an angle 2 with respect to the horizontal orientation of the blade 100, as defined by the mounting surface 3 of the blade. The angle 2 is such that the top of cutting surface 1 is forward of the bottom of the cutting surface. In one embodiment the angle 2 is between about 30 and about 45 degrees. In a particular embodiment, the angle 2 is between about 30 and about 40 degrees. In another particular embodiment, the angle 2 is between about 33 and about 39 degrees. In a more particular embodiment, the angle 2 is about 36 degrees.

In some embodiments, the upper end 4 of the cutting surface 1 is radiused. The radiused upper end 4 of the cutting surface 1 is about 90 degrees of a circle and has a radius measurement between about 0.50 mm and 1.50 mm. In a particular embodiment, the radius is about 0.94 mm.

In some embodiments, the upper cutting surface 1 has a vertical height 5 between about 0.70 mm and about 1.30 mm. In particular embodiments, the vertical height 5 is between about 0.85 mm and 1.15 mm. In a more particular embodiment, the vertical height 5 is about 1.04 mm. In particular embodiments, the lower end of the upper cutting surface 1 may be even with or extend below the plane defined by the mounting surface 3 of the blade. In particular embodiments, the lower end of the upper cutting surface 1 extends between about 0.05 and 0.15 mm below the plane defined by the mounting surface 3 of the blade. In further embodiments, the lower end of the upper cutting surface 1 extends between about 0.08 and 0.12 mm below the plane defined by the mounting surface 3 of the blade. In more particular embodiments, the lower end of the upper cutting surface 1 extends about 0.1 mm below the plane defined by the mounting surface 3 of the blade.

In a particular embodiment, the blade 100 as shown in FIG. 1A comprises a lower cutting surface 6 on the leading end of the blade, which is at an angle 7 with respect to the horizontal orientation of the blade 100, as defined by the mounting surface 3 of the blade. The angle 7 is such that the bottom of the lower cutting surface 6 is forward of the top of the lower cutting surface. In one embodiment the angle 7 is between about 45 and about 65 degrees. In a particular embodiment, the angle 7 is between about 50 and about 60 degrees. In a more particular embodiment, the angle 7 is about 54 degrees.

In some embodiments, the lower cutting surface 6 has a vertical height 8 between about 0.50 mm and about 1.00 mm. In particular embodiments, the vertical height 8 is between about 0.60 mm and 0.90 mm. In a more particular embodiment, the vertical height 8 is about 0.76 mm. In particular embodiments, the upper end of the lower cutting surface 6 may be even with or is below the plane defined by the mounting surface 3 of the blade. In particular embodiments, the upper end of the lower cutting surface 6 is between about 0.05 and 0.15 mm below the plane defined by the mounting surface 3 of the blade. In further embodiments, the upper end of the lower cutting surface 6 is between about 0.08 and 0.12 mm below the plane defined by the mounting surface 3 of the blade. In more particular embodiments, the upper end of the lower cutting surface 6 is about 0.1 mm below the plane defined by the mounting surface 3 of the blade.

In a particular embodiment, the blade as shown in FIG. 1A comprises upper and lower cutting surfaces on the leading end of the blade, which are at an angle 9 to one another and meet at a central crotch 10. In one embodiment the angle 9 is between about 80 and about 100 degrees. In a further embodiment, the angle 9 is between about 85 and about 95 degrees. In a still further embodiment, the angle 9 is about 90 degrees.

In some embodiments, the plane where the upper and lower cutting surfaces meet is angled downward 11 towards the crotch 10. In some embodiments, the angle 11, as it relates to the plane defined by the mounting surface 3 of the blade, is between about 0 and 20 degrees. In further embodiments, the angle 11, as it relates to the plane defined by the mounting surface 3 of the blade, is between about 5 and 19 degrees. In a particular embodiment, the angle 11, as it relates to the plane defined by the mounting surface 3 of the blade, is about 9 degrees.

In a particular embodiment, the total length 12 of the blade from the leading point of the upper cutting surface 1 to the trailing end of the blade is between about 12 mm and about 20 mm. In another particular embodiment, the total length 12 of the blade from the leading point of the upper cutting surface 1 to the trailing end of the blade is between about 14 mm and about 18 mm. In a more particular embodiment the total length 12 of the blade is about 16.69 mm. In a particular embodiment, the length 12a of the forward section of the blade from the leading point of the upper cutting surface 1 to the leading edge of the notch 13 is between about 2 mm and about 8 mm. In another particular embodiment, the length 12a of the forward section of the blade from the leading point of the upper cutting surface to the leading edge of the notch 13 is between about 3 mm and about 5 mm. In a more particular embodiment the length 12a of the forward section of the blade is about 3.99 mm.

In a particular embodiment, the horizontal length 12b of the blade from the distal end notch 13 to the foremost point of the lower cutting surface 6 is between about 1.0 mm and about 5.0 mm. In a further embodiment, the horizontal length 12b of the blade from the distal end notch 13 to the foremost point of the lower cutting surface 6 is between about 2.0 mm and about 4.0 mm. In a still further embodiment, the horizontal length 12b of the blade from the distal end notch 13 to the foremost point of the lower cutting surface 6 is about 2.72 mm.

In a particular embodiment, the horizontal length 12c of the blade from the distal end notch 13 to the most proximal point of the trailing edge 6 of the blade is between about 9.0 mm and about 16.0 mm. In a further embodiment, the horizontal length 12c of the blade from the distal end notch 13 to the most proximal point of the trailing edge 6 of the blade is between about 11.0 mm and about 14.0 mm. In a still further embodiment, the horizontal length 12c of the blade from the distal end notch 13 to the most proximal point of the trailing edge 6 of the blade is about 12.7 mm.

In order to insure that, during manufacture, the blade is consistently joined to the knife tube in the same location, the lower surface of the main body of the blade comprises a transition 14, the distal end of which meets the notch 13 in the lower surface of the main body of the blade. During assembly of the endoscopic knife assembly, the mounting surface 3 is aligned with and positioned on the forward end of the knife tube. Following the positioning of the blade on the knife tube, the blade is laser welded all around to the knife tube. In a particular embodiment, the strength of the weld is tested by applying torque to the unit, for example about 10 in-lbs of torque. In an one embodiment, the depth of the transition 14 is between about 0.03 mm and about 0.18 mm. In a particular embodiment, the depth of the transition 14 is between about 0.05 mm and about 0.15 mm. In a more particular embodiment, the depth of the transition 14 is about 0.10 mm.

In particular embodiments, the blade further comprises a notch 13 on the lower edge of the blade between the mounting surface 3 and the forward section of the blade 12a. In particular embodiments, the notch 13 is relatively semi-circular in shape, having a radius of between about 0.1 mm and about 0.3 mm, more particularly about 0.18 mm. The top of the notch 13 is recessed 15 into the body of the blade, with respect to the mounting surface 3, between about 0.1 mm and about 0.3 mm, more particularly about 0.18 mm.

In particular embodiments, the horizontal distance 16 between the crotch 10 and the notch 13 can be different, dependent upon the application for the blade. In some embodiments, the horizontal distance is between about 1 mm and about 4 mm. In other embodiments, the horizontal distance 16 is between about 1.5 mm and about 3.5 mm. In a more particular embodiment, the horizontal distance 16 is about 2.24 mm, as exemplified in FIG. 1A.

In order to prevent the blade from catching on tissues or a cannula when the blade is drawn backwards through a cannula tube, the trailing edge 17 of the blade is angled down to the knife tube and the top of the trailing edge 17 is radiused 18. In a particular embodiment, the vertical height of the trailing edge 17 is between about 0.50 mm and about 0.88 mm, more particularly about 0.60 mm to about 0.70 mm. In a more particular embodiment, the vertical height of the trailing edge 17 is about 0.66 mm. In some embodiments, the radius of the radiused edge 18 at the top of the trailing edge 17 is between about 0.40 mm and about 0.80 mm. In further embodiments, the radius of the radiused edge 18 at the top of the trailing edge 17 is between about 0.50 mm and about 0.70 mm, more particularly about 0.61 mm.

In some embodiments the trailing edge 17 is canted forward at an angle 19 with respect to the horizontal line of the mounting surface 3. In particular embodiments, the forward angle 19 of the trailing edge 17 is between about 30 degrees and about 90 degrees. In further embodiments, the angle 19 is between about 45 degrees and about 85 degrees.

In more particular embodiments, the angle 19 is between about 65 degrees and about 80 degrees. In a most particular embodiment, the angle 19 is about 75 degrees.

In some embodiments, the top edge 20 of the blade 100 forms an angle 21 with respect to the mounting surface 3, sloping downward as defined by FIG. 1A from where it meets the radiused upper end 4 at the top of cutting surface 1 to where it meets the radius 18 at the top of the trailing edge 17. In particular embodiments, the angle 21 of the top edge 20 is between about 2.5 degrees and about 10 degrees. In more particular embodiments, the angle 21 of the top edge 20 is between about 3.5 degrees and about 7 degrees. In a still more particular embodiment, the angle 21 of the top edge is about 5 degrees.

Referring now to FIG. 1B, the upper cutting surface 1 is a single beveled cutting surface and the angle 22 is between about 30 degrees and about 50 degrees. In some embodiments, the angle 22 is between about 35 degrees and about 45 degrees. In a particular embodiment, the angle 22 is about 40 degrees. While not shown in the figure, the lower cutting surface 6 is a similarly a single beveled cutting surface and the angle is between about 30 degrees and about 50 degrees. In some embodiments, the angle is between about 35 degrees and about 45 degrees. In a particular embodiment, the angle is about 40 degrees.

Also referring to FIG. 1B, in some embodiments, the depth of the grind 23 of upper cutting surface 1, as well as for lower cutting surface 6, is between about 0.6 mm and about 1.0 mm. In other embodiment, the depth of the grind 23 is between about 0.7 mm and about 0.9 mm. In a further embodiment, the depth of the grind 23 is about 0.86 mm.

Referring to FIG. 1C, in a particular embodiment, the overall height 24 of the body of the blade 100 is between about 2.0 mm and about 3.6 mm. In another embodiment, the height 24 of the body of the blade is between about 2.4 mm and about 3.2 mm. In a particular embodiment, the height 24 of the body of the blade is between about 2.6 mm and about 3.0 mm. In a more particular embodiment, the height 24 of the body of the blade is about 2.84 mm.

Again referring to FIG. 1C, in a particular embodiment, the width 25 of the body of the blade is between about 0.3 mm and about 0.9 mm. In another embodiment, the width 25 of the body of the blade is between about 0.45 mm and about 0.75 mm. In a particular embodiment, the width 25 the body of the blade is about 0.64+/−0.25 mm.

FIG. 2A depicts a side view of another embodiment the blade component of the endoscopic knife assembly, showing the upper and lower cutting surfaces at the leading end of the blade, the transition where the blade is joined to the knife tube and the taper at the trailing end of the blade.

FIG. 2B is an view depicting an exemplary angle of the cutting surface of the blade as viewed from the perspective of the line B-B in FIG. 2A.

FIG. 2C is a perspective view of the blade in FIG. 2A from the back depicting the height and width of the blade.

FIG. 2D is a perspective view of the blade in FIG. 2A from the top depicting the length of the blade.

FIG. 2E is a perspective view of the blade in FIG. 2A from the back depicting the height and width of the blade.

In a particular embodiment, the blade 100 as shown in FIG. 2A comprises an upper cutting surface 1 on the leading end of the blade, which is at an angle 2 with respect to the horizontal orientation of the blade 100, as defined by the mounting surface 3 of the blade. The angle 2 is such that the top of cutting surface 1 is forward of the bottom of the cutting surface. In one embodiment the angle 2 is between about 30 and about 45 degrees. In a particular embodiment, the angle 2 is between about 30 and about 40 degrees. In another particular embodiment, the angle 2 is between about 33 and about 39 degrees. In a more particular embodiment, the angle 2 is about 36 degrees.

Referring now to FIG. 2B, the lower cutting surface 6 is a single beveled cutting surface and the angle 22 is between about 30 degrees and about 50 degrees. In some embodiments, the angle 22 is between about 35 degrees and about 45 degrees. In a particular embodiment, the angle 22 is about 40 degrees. While not shown in the figure, the upper cutting surface 1 is a similarly a single beveled cutting surface and the angle is between about 30 degrees and about 50 degrees. In some embodiments, the angle is between about 35 degrees and about 45 degrees. In a particular embodiment, the angle is about 40 degrees.

Also referring to FIG. 2B, in some embodiments, the depth of the grind 23 of lower cutting surface 6, as well as for upper cutting surface 1, is between about 0.6 mm and about 1.0 mm. In other embodiment, the depth of the grind 23 is between about 0.7 mm and about 0.93 mm. In a further embodiment, the depth of the grind 23 is about 0.89 mm.

Referring to FIG. 2C, in a particular embodiment, the overall height 24 of the body of the blade 100 is between about 2.5 mm and about 4.5 mm. In another embodiment, the height 24 of the body of the blade is between about 3 mm and about 4 mm. In a particular embodiment, the height 24 of the body of the blade is between about 3.2 mm and about 3.8 mm. In a more particular embodiment, the height 24 of the body of the blade is about 3.51 mm.

Again referring to FIG. 2C, in a particular embodiment, the width 25 of the body of the blade is between about 0.3 mm and about 0.9 mm. In another embodiment, the width 25 of the body of the blade is between about 0.45 mm and about 0.75 mm. In a particular embodiment, the width 25 the body of the blade is about 0.64+/−0.25 mm.

Referring now to FIG. 2D, in a particular embodiment, the total length 12 of the blade from the leading point of the upper cutting surface 1 to the trailing end of the blade is between about 13 mm and about 21 mm. In another particular embodiment, the total length 12 of the blade from the leading point of the upper cutting surface 1 to the trailing end of the blade is between about 15 mm and about 19 mm. In a more particular embodiment the total length 12 of the blade is about 17.09 mm.

FIG. 2E is an illustration depicting the blade 100 viewed at an angle.

In some embodiments, the blade 100 is affixed onto a knife tube, such as, but not limited to, those exemplified in FIGS. 3A-F and FIGS. 4A-E.

Figure 3A:
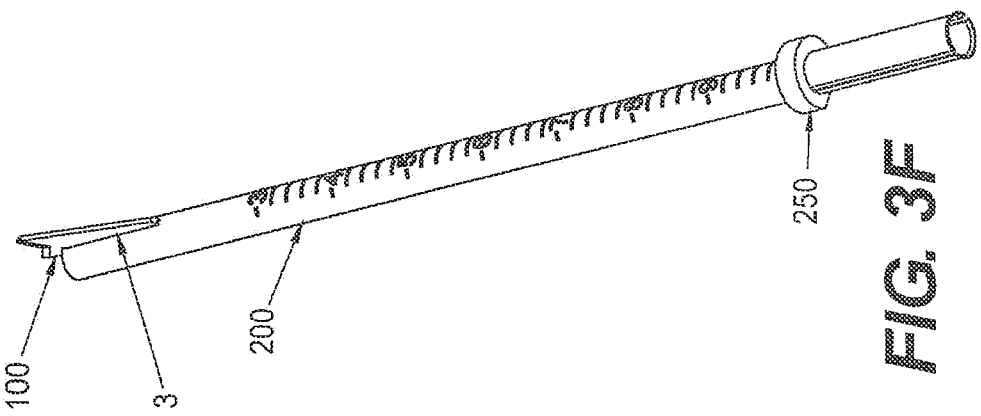
FIGS. 3A-F illustrate an endoscopic knife assembly.

FIGS. 3A-F show an endoscopic assembly with a blade 100 mounted on a knife tube 200. As shown in FIG. 3A, the blade 100 is attached to the knife tube 200 having an alignment ring 250, such that the blade 100 is welded to the knife tube 200.

Figure 3B:

The knife tube 200 can optionally be marked on the top or side surface with gradations as exemplified in FIG. 3B to show the distance 41 to the distal end of the knife tube, or to a specific point on the leading edge of the cutting surface. As a non-limiting example, major gradations 42 can be made to show each centimeter in distance from the distal end of the knife tube, with minor gradations 43 between them to, for example, show each 1, 2, 2.5 or 5 millimeters. While the gradations can be applied to the knife tube 200 by any means known in the art, it is preferable to lasermark the gradations on the knife tube 200 for accuracy and permanence. Additionally, the knife tube 200 can also be marked in a similar manner with additional information, for example on the bottom or a side surface of the knife tube 200. Exemplary markings may include, but are not limited to, a maker's mark, part number, lot number and an indication that the endoscopic knife assembly is intended for only a single use.

Figure 3C:
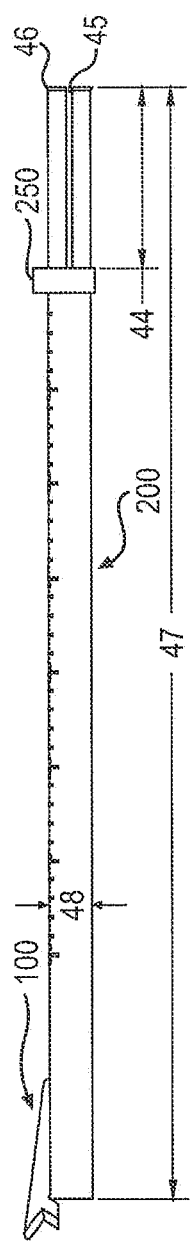

Referring to FIG. 3A-C, showing side, top and bottom views of the endoscopic knife assembly, an alignment ring 250 is affixed near the proximate end of the knife tube 200. In one embodiment, the alignment ring 250 is affixed in position on the knife tube 200 using USP Class VI gamma irradiation and steam resistant epoxy adhesive during assembly. In some embodiments, a two part epoxy such as MASTERBOND EP42 HT™ or ARMSTRONG C-7™, or a suitable equivalent thereof is used. In one embodiment, the distance 44 between the alignment ring 250 and the proximate end of the knife tube 200 is between about 15 mm and about 25 mm. In another embodiment, the distance 44 is between about 18.9 mm and about 19.66 mm. In another embodiment, the distance 44 is about 19.28+/−0.38 mm.

As shown in FIGS. 3A-F, in particular embodiments, the alignment ring 250 comprises a flattened surface 252 that is aligned on the opposite side of the knife tube 200 as the blade 100. The plane of the flattened surface 252 of the alignment ring 250 is oriented perpendicular to the plane in which the blade is affixed to the knife tube 200.

The knife tube further comprises slots 45 in the proximate end that are positioned on the sides of the knife tube 200, perpendicular to the blade mounted on the top of the knife tube. The slots 45 in particular embodiments extend forward to where the alignment ring 250 is affixed to the knife tube 200. In some applications, the slots 45 may not extend forward to where the alignment ring 250 is affixed to the knife tube 200. In one embodiment, the slots 45 have a width of between about 0.4 mm and about 1.1 mm wide, more particularly between about 0.53 mm and about 0.91 mm wide. Most particularly, the width of the slots 45 is about 0.66 mm.

The slots and alignment ring provide an attachment point for a locking device, in order to mount an endoscope to the scope-mounting blade or endoscopic knife assembly.

Again referring to FIG. 3A, in a particular embodiment, the total length 47 of the knife tube 200 is between about 60 mm and about 160 mm. In a further embodiment, the total length 47 of the knife tube 200 is between about 75 mm and about 145 mm. In a still further embodiment, the total length 47 of the knife tube 200 is between about 90 mm and about 130 mm. In a more particular embodiment, the total length 47 of the knife tube 200 is about 116.8 mm.

Also referring to FIG. 3A, in a particular embodiment, the width or outer diameter 48 of the knife tube is such that it will fit and slide easily within a cannula having an inner diameter of about 4 mm, yet will be held securely by said cannula, such that the knife tube does not experience significant side-to-side and/or up-and-down play.

Referring to FIGS. 3A-C and F, in some embodiments, the knife tube 200 has a flared proximate end 46. In one embodiment, about 0.2 to about 0.5 most proximate millimeters of the knife tube 200 are flared. In another embodiment, about the 0.38 most proximate millimeters of the knife tube 200 are flared. In another embodiment, the flared proximate end 46 has a flare angle of about 20 to 40 degrees, more particularly about 30 degrees. In still another embodiment, the outer diameter of the flared proximate end 46 of the knife tube is about 0.25 mm to about 0.45 mm, more particularly about 0.36 mm to about 0.37 mm.

Figure 3D:
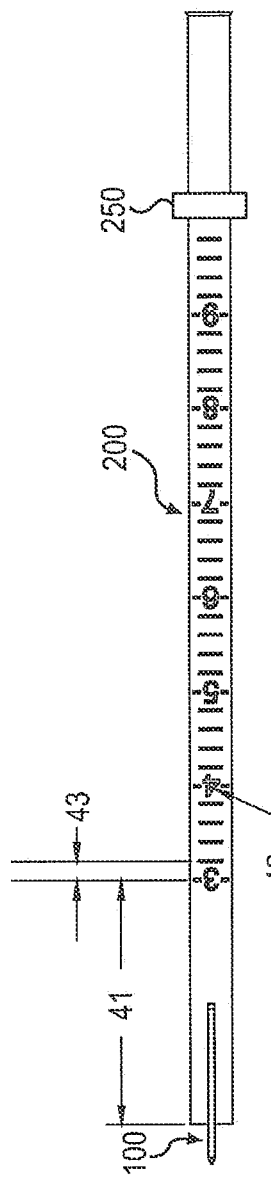
Figure 3E:
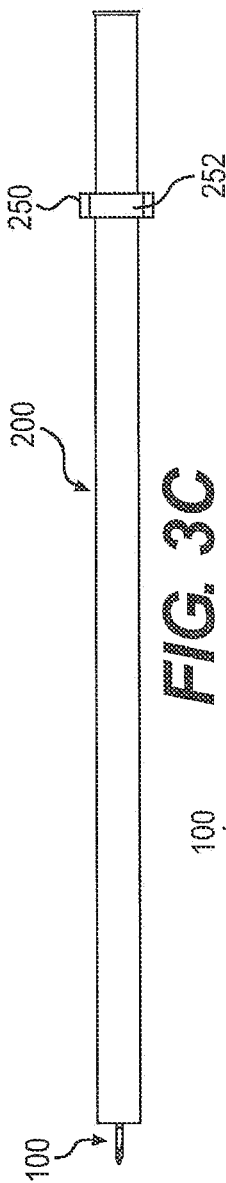

Referring now to FIG. 3D, viewing the endoscopic knife assembly from the distal end and FIG. 2E, viewing the endoscopic knife assembly from the proximate end, the inner diameter of the knife tube 200 is such that an endoscope or arthroscope camera can be inserted into the knife tube in order to show the blade and the target tissue during a procedure.

Figure 3F:

FIG. 3F is an illustration depicting the endoscopic knife assembly viewed at an angle and showing the mounting surface 3 of the blade 100 welded onto the knife tube 200.

FIGS. 4A-E show another embodiment of an endoscopic assembly with a blade 100 mounted on a knife tube 200. As shown in FIG. 4A, the blade 100 is attached to the knife tube 200 having an alignment ring 250, such that the blade 100 is welded to the knife tube 200.

The knife tube 200 can optionally be marked on the top or side surface with gradations as exemplified in FIG. 4B to show the distance 41 to the distal end of the knife tube, or to a specific point on the leading edge of the cutting surface. As a non-limiting example, major gradations 42 can be made to show each centimeter in distance from the distal end of the knife tube, with minor gradations 43 between them to, for example, show each 1, 2, 2.5 or 5 millimeters. While the gradations can be applied to the knife tube by any means known in the art, it is preferable to lasermark the gradations on the knife tube 200 for accuracy and permanence. Additionally, the knife tube 200 can also be marked in a similar manner with additional information, for example on the bottom or a side surface of the knife tube 200. Exemplary markings may include, but are not limited to, a maker's mark, part number, lot number and an indication that the endoscopic knife assembly is intended for only a single use.

Referring to FIG. 4A-C, showing side, top and bottom views of the endoscopic knife assembly, an alignment ring 250 is affixed near the proximate end of the knife tube 200. In one embodiment, the alignment ring 250 is affixed in position on the knife tube 200 using USP Class VI gamma irradiation and steam resistant epoxy adhesive during assembly. In some embodiments, a two part epoxy such as MASTERBOND EP42 HT™ or ARMSTRONG C-7™, or a suitable equivalent thereof is used. In one embodiment, the distance 44 between the alignment ring 250 and the proximate end of the knife tube 200 is between about 15 mm and about 25 mm. In another embodiment, the distance 44 is between about 18.9 mm and about 19.66 mm. In another embodiment, the distance 44 is about 19.28+/−0.38 mm.

As shown in FIGS. 4A-E, in particular embodiments, the alignment ring 250 comprises a flattened surface 252 that is aligned on the opposite side of the knife tube 200 as the blade 100. The plane of the flattened surface 252 of the alignment ring 250 is oriented perpendicular to the plane in which the blade is affixed to the knife tube 200.

The knife tube further comprises slots 45 in the proximate end that are positioned on the sides of the knife tube 200, perpendicular to the blade mounted on the top of the knife tube. The slots 45 in particular embodiments extend forward to where the alignment ring 250 is affixed to the knife tube 200. In some applications, the slots 45 may not extend forward to where the alignment ring 250 is affixed to the knife tube 200. In one embodiment, the slots 45 have a width of between about 0.4 mm and about 1.1 mm wide, more particularly between about 0.53 mm and about 0.91 mm wide. Most particularly, the width of the slots 45 is about 0.66 mm.

The slots and alignment ring provide an attachment point for a locking device, in order to mount an endoscope to the scope-mounting blade or endoscopic knife assembly.

Again referring to FIG. 4A, in a particular embodiment, the total length 47 of the knife tube 200 is between about 50 mm and about 150 mm. In a further embodiment, the total length 47 of the knife tube 200 is between about 75 mm and about 125 mm. In a still further embodiment, the total length 47 of the knife tube 200 is between about 90 mm and about 110 mm. In a more particular embodiment, the total length 47 of the knife tube 200 is about 100 mm.

Also referring to FIG. 4A, in a particular embodiment, the width or outer diameter 48 of the knife tube is such that it will fit and slide easily within a cannula having an inner diameter of about 2.7 mm, yet will be held securely by said cannula, such that the knife tube does not experience significant side-to-side and/or up-and-down play.

Referring to FIGS. 4A-C and E, in some embodiments, the knife tube 200 has a flared proximate end 46. In one embodiment, about 0.2 to about 0.5 most proximate millimeters of the knife tube 200 are flared. In another embodiment, about the 0.38 most proximate millimeters of the knife tube 200 are flared. In another embodiment, the flared proximate end 46 has a flare angle of about 20 to 40 degrees, more particularly about 30 degrees. In still another embodiment, the outer diameter of the flared proximate end 46 of the knife tube is about 0.25 mm to about 0.45 mm, more particularly about 0.36 mm to about 0.37 mm.

Referring now to FIG. 4D, viewing the endoscopic knife assembly from the distal end, the inner diameter of the knife tube 200 is such that an endoscope or arthroscope camera can be inserted into the knife tube in order to show the blade and the target tissue during a procedure.

FIG. 4E is an illustration depicting the endoscopic knife assembly viewed at an angle and showing the mounting surface 3 of the blade 100 welded onto the knife tube 200.

Another aspect of the present application relates to an instrument kit for implementing an endoscopic surgical procedure. The instrument kit contains an endoscopic knife assembly having a low-profile blade having an upper cutting surface and a lower cutting surface. In some embodiments, the instrument kit comprises components and implements useful for endoscopic procedures. In one embodiment, the instrument kit contains a cannula. In a related embodiment, the cannula is transparent. In another related embodiment, the cannula includes a longitudinal bore having open proximal and distal ends and an open slot extending along the length thereof communicating with the open ends. In another related embodiment, the instrument kit include an elongate insertion member, such as an obturator, that is slidably receivable within the cannula guide member and is configured so that at least portions thereof conform with the open distal end and the open slot of the guide member to form a smooth exterior surface in combination therewith.

In one embodiment, the instrument kit further includes an endoscope sized for insertion into the cannula guide member for direct visualization of an operative site.

In one embodiment, the instrument kit further includes an endoscope sized for insertion into the cannula guide member for direct visualization of an operative site.

In another embodiment, the endoscope is capable to carry a cutting instrument at a leading end. The endoscope is insertable into the cannula guide member such that the cutting instrument protrudes through the open slot in the cannula guide member.

In another embodiment, the instrument kit further includes an elevator.

In another embodiment, the instrument kit further includes a depth gauge mountable to a leading end of the endoscope.

In another embodiment, the instrument kit further includes a locking device capable of locking the endoscope and the cannula guide member into mutually fixed positions.

In another embodiment, the instrument kit further includes a stop device mountable on the cannula guide member to prevent excessive penetration at a surgical site by the cutting instrument. In another embodiment, the instrument kit further includes a curved dissector.

Methods

Another aspect of the present application relates to a method for uniportal endoscopic surgery. Uniportal endoscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner.

The uniportal endoscopic surgical procedure described herein can be used to implement a number of different surgical procedures. In some embodiments, the uniportal endoscopic surgical procedure is selected from the group consisting of trigger finger release, carpal tunnel release, cubital tunnel release, plantar fascia release, lateral release for patella realignment, release of the extensor tendons, release of the posterior and other compartments of the leg, and forearm fascial release.

One embodiment of the present application relates to a method for a performing a uniportal endoscopic surgical procedure a target tissue in a subject. Generally, following the establishment of an entry portal, in some embodiments a blunt instrument, such as an elevator is inserted through the portal to establish an opening in the underlying tissue between the portal and the target tissue.

A cannula having open proximal and distal ends and an open slot extending along the length of the cannula is inserted into the entry portal and extended through to the target tissue. In particular embodiments, the cannula is made of a clear plastic material so that the entirety of the surrounding tissue can be viewed with an arthroscope. In order to facilitate insertion of the cannula, the central lumen of the cannula comprises an obturator, which is withdrawn following insertion of the cannula.

In some embodiments, the cannula has an inner diameter of between about 2.0 mm to about 3.5 mm. In further embodiments, the cannula has an inner diameter of between about 2.4 mm to about 3.0 mm. In a particular embodiment, the cannula has an inner diameter of about 2.7 mm.

In some other embodiments, the cannula has an inner diameter of between about 3.3 mm to about 4.7 mm. In further embodiments, the cannula has an inner diameter of between about 3.7 mm to about 4.3 mm, in a particular embodiment, the cannula has an inner diameter of about 4.0 mm.

An arthroscope is inserted into the cannula to view the target tissue and the surrounding tissues, assuring that the slot of the cannula is in proper orientation to the target tissue. The arthroscope is withdrawn and an arthroscope with a mounted endoscopic knife assembly having a low-profile blade that has upper and lower cutting surfaces that is radiused at its upper end is advanced into the cannula, with the knife blade aligned with the slot of the cannula. In some embodiments, the arthroscope used for viewing the target tissue and the surrounding tissues is the same unit as the arthroscope comprising a mounted endoscopic knife assembly. In other embodiments, the arthroscope used for viewing the target tissue and the surrounding tissues is a different unit from the arthroscope comprising a mounted endoscopic knife assembly.

The arthroscope comprising a mounted endoscopic knife assembly is advanced further through the cannula so that the blade moves in contact with the target tissue through the slot, operatively engaging the target tissue with the blade. The blade is further advanced through the cannula to divide the target tissue.

In one particular embodiment, the operative procedure is trigger finger release.

In another particular embodiment, the establishing an entry portal comprises making an incision.

In another particular embodiment, the target tissue is the A1 pulley.

In another particular embodiment, the inserting of said arthroscope comprising an endoscopic knife assembly having a low-profile blade that has an upper cutting surface and a lower cutting surface is followed by the insertion of an arthroscope comprising a means for visualization of the results of the endoscopic surgical procedure on the target tissue.

The present invention is further illustrated by the following examples which should not be construed as limiting. The contents of all references, patents and published patent applications cited throughout this application, as well as the Figures and Tables, are incorporated herein by reference.

Example 1: Uniportal Endoscopic Trigger Release

In a patient presenting with trigger finger of the middle or ring finger, a 1 cm incision is made just proximal to the A1 pulley on the distal palmar crease proximate to the affected digit.

An elevator is introduced into the incision and used to create a plane superficial to the flexor tendon sheath. The elevator is withdrawn.

A slotted cannula with an obturator inserted therein is introduced into the incision and advanced through the plane created by the elevator. The slot of the cannula is oriented facing the flexor tendon sheath. The obturator is removed from the cannula.

Figures 5A, 5B:
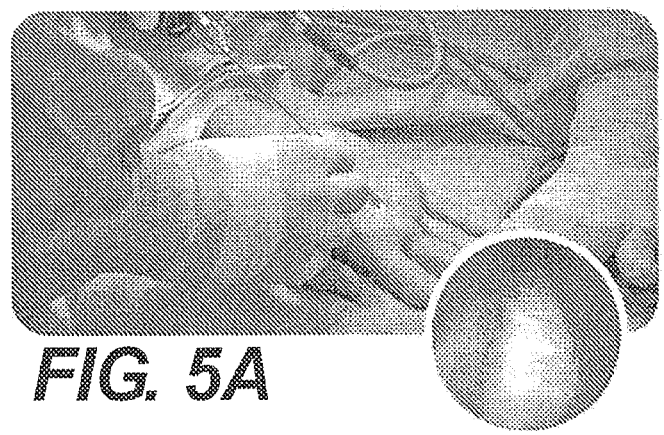
FIGS. 5A-B depict the visualization of the A1 and A2 pulleys in a uniportal endoscopic trigger finger release surgical procedure.

An arthroscope is introduced into the cannula and advanced to visualize the A1 pulley and A2 pulley as shown in FIGS. 5A-B. The arthroscope is withdrawn.

An endoscopic knife assembly having a low-profile blade having an upper cutting surface and a lower cutting surface is fastened onto an arthroscope.

Figures 6A, 6B:
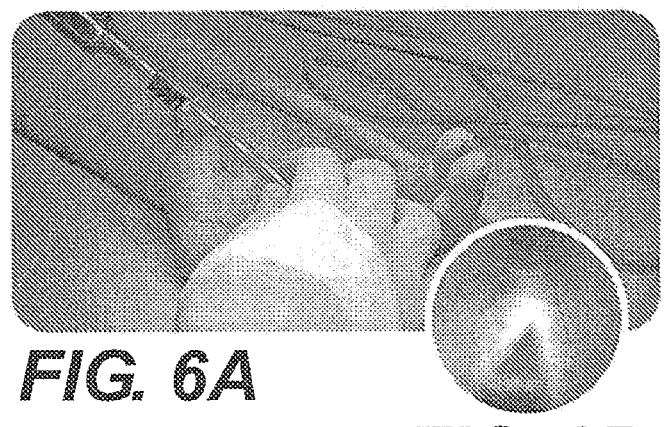
FIGS. 6A-B depict the direct viewing of the division of the A1 pulley during a uniportal endoscopic trigger finger release surgical procedure.

The scope and blade assembly is advanced into the cannula, dividing the A1 pulley. Having the endoscopic knife assembly mounted directly on the arthroscope allows direct visualization of the procedure from the point-of-view of the blade, allowing visualization of the A2 pulley and avoiding damage to the A2 pulley (FIGS. 6A-B). The scope and blade assembly is withdrawn from the cannula.

Figures 7A, 7B:
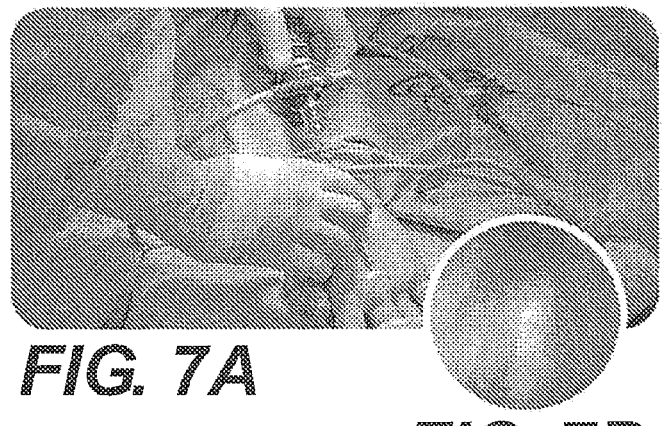
FIGS. 7A-B depict the visualization of the cut ends of the A1 pulley and of the underlying flexor tendon during a uniportal endoscopic trigger finger release surgical procedure.

An arthroscope is again advanced into the cannula to visualize the cut edges of the A1 pulley, as well as visualization of the underlying flexor tendon (FIGS. 7A-B).

While visualizing the tendon, release of the tendon is confirmed by passive manipulation of the digit through its range of motion.

The absence of triggering is confirmed by having the subject flex and extend the affected digit.

The arthroscope is withdrawn and the cannula is removed from the incision.

The wound is closed and a soft bandage is applied.

The patient is encouraged to begin early finger motion following surgery and to resume daily activities as tolerated.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for treating trigger finger, comprising:
    establishing an entry portal at a location proximal to A1 pulley;
    inserting a cannula having open proximal and distal ends and an open slot extending along the length of the cannula;
    inserting an endoscope into the cannula, said endoscope comprising an endoscopic knife assembly having a low-profile blade, wherein the low-profile surgical blade comprises a proximal end, a distal end, a top edge, a lower edge, an upper cutting surface and a lower cutting surface at the distal end, a non-cutting radiused surface at a top end of the upper cutting surface, and a horizontal mounting surface at the lower edge, wherein the upper cutting surface and the lower cutting surface meet at a crotch therebetween, wherein the blade is sized to fit at a tip of an endoscope, wherein the blade comprises a notch on the lower edge that is in contact with a surgical tube, and wherein the notch is concave, substantially crescent-shaped, and is recessed from the horizontal mounting surface and into a body of the blade;
    advancing said endoscope so that the blade moves in contact with the A1 pulley through the slot;
    operatively engaging the A1 pulley with the blade; and
    advancing the blade through the cannula to divide the A1 pulley.

2. The method of claim 1, wherein the step of inserting an endoscope comprising an endoscopic knife assembly is preceded by the insertion of another endoscope to visualize anatomic structures surrounding the cannula.

3. The method of claim 1, wherein the crotch is angled downward from the proximal end of the blade towards the distal end of the blade.

4. The method of claim 1, wherein the top surface of the blade is angled downward towards the proximal end of the blade.

5. The method of claim 1, wherein the upper cutting surface of the blade is angled about 30-40 degrees from a horizontal plane running through the crotch.

6. The method of claim 5, wherein the upper cutting surface of the blade is angled about 36 degrees from a horizontal plane running through the crotch.

7. The method of claim 1, wherein the lower cutting surface of the blade is angled about 50-60 degrees from a horizontal plane running through the crotch.

8. The method of claim 7, wherein the lower cutting surface of the blade is angled about 54 degrees from a horizontal plane running through the crotch.

9. The method of claim 1, wherein the upper cutting surface of the blade and the lower cutting surface of the blade meet at a downward angle at the crotch.

10. The method of claim 1, wherein the surgical tube comprises a distal end and a proximal end and wherein the low-profile blade is mounted on the distal end of the surgical tube.

11. The method of claim 10, wherein the endoscopic knife assembly further comprising a handle at the proximal end of the surgical tube.

12. The method of claim 10, wherein the surgical tube comprises an alignment ring attached near the proximal end and one or more slots at the proximal end for the attachment of a locking assembly to the surgical tube and alignment ring.

13. The method of claim 1, wherein the surgical tube is marked on the top or side surface with gradations.

14. The method of claim 1, wherein the blade is welded to the surgical tube.

* * * * *